United States Patent [19]

El-Rashidy

[11] Patent Number: 6,087,362

[45] Date of Patent: Jul. 11, 2000

[54] APOMORPHINE AND SILDENAFIL COMPOSITION

[75] Inventor: Ragab El-Rashidy, Deerfield, Ill.

[73] Assignee: Pentech Pharmaceuticals, Inc., Buffalo Grove, Ill.

[21] Appl. No.: 09/270,035

[22] Filed: Mar. 16, 1999

[51] Int. Cl.⁷ .......................... A61K 31/495; A61K 31/44
[52] U.S. Cl. ............................................ 514/253; 514/284
[58] Field of Search ...................................... 514/284, 253

[56] References Cited

U.S. PATENT DOCUMENTS 5,256,652  10/1993  El-Rashidy ................................. 514/58
5,770,606   6/1998  El-Rashidy et al. ..................... 514/284

OTHER PUBLICATIONS

Leland, J., "A Pill for Impotence?," *Newsweek*, pp. 62–68, (Nov. 17, 1997).
Goldstein et al., "Oral Sildenafil in the Treatment of Erectile Dysfunction", *The New England Journal of Medicine*, 338(20), pp. 1397–1404 (1998).
Handy B., "The Viagra™ Craze," *Time*, pp. 50–57 (May 4, 1998).
Valdes–Rodriguez A., "Viagra for her," *Chicago Tribune*, Womanews Section 13, p. 7 (Dec. 20, 1998).
Wilson E., "Impotence Drugs: More than Viagra," *C&EN*, pp. 29–33 (Jun. 29, 1998).
Japsen B., "Impotency drug trials promising for Abbott," *Chicago Tribuen*, Business Section, pp. 1–2 (Sep. 4, 1998).
Kaplan S. et al., "Combination Therapy Using Oral Alpha–Blockers and Intracavernosal Injection in Men With Erectile Dysfunction," *Urology* 52(5), pp. 739–743 (1998).
Utiger R., "A Pill for Impotence," *The New England Journal of Medicine*, 338(20), pp. 1458–1459 (May 14, 1998).
VIAGRA™, Prescription Information published by PRO–MARK® Pharmacies, http://www.pro–mark–pharmacies.com/viagra.html (May 8, 1998).

*Primary Examiner*—Raymond Henley, III
*Attorney, Agent, or Firm*—Olson & Hierl, Ltd.

[57] ABSTRACT

The treatment of sexual dysfunction in human patients by an oral therapy regimen of administration of apomorphine and sildenafil is disclosed. This treatment optimizes the efficacy of each drug and substantially minimizes the undesirable side effects associated individually therewith. Apomorphine and sildenafil can be co-administered with a combination dosage unit or administered sequentially in separate dosage units, substantially prior to sexual activity. Other erectogenic agents can be administered along with apomorphine and sildenafil.

20 Claims, No Drawings

APOMORPHINE AND SILDENAFIL COMPOSITION

FIELD OF THE INVENTION

This invention relates to compositions, dosage forms and methods for treating sexual dysfunction in humans. More particularly, this invention relates to the use of compositions containing apomorphine and sildenafil.

BACKGROUND OF THE INVENTION

A normal erection occurs as a result of a coordinated vascular event in the penis. This is usually triggered neurally and consists of vasodilation and smooth muscle relaxation in the penis and its supplying arterial vessels. Arterial inflow causes enlargement of the substance of the corpora cavernosa. Venous outflow is trapped by this enlargement, permitting sustained high blood pressures in the penis sufficient to cause and maintain rigidity. Muscles in the perineum also assist in creating and maintaining penile rigidity. Erections are induced centrally in the nervous system by sexual thoughts, fantasy, and/or stimulation and can be reinforced locally by reflex mechanisms (e.g., tactile stimulation).

Impotence or male erectile dysfunction is defined as an inability to achieve and sustain an erection sufficient for satisfactory sexual performance and intercourse. Impotence in any given case can result from psychological disturbances (psychogenic), from physiological abnormalities in general (organic), from neurological disturbances (neurogenic), hormonal deficiencies (endocrine) or from a combination of the foregoing.

As used herein, psychogenic impotence is defined as functional impotence with no apparent overwhelming organic basis. It may be characterized by an ability to have an erection in response to some stimuli (e.g., masturbation, spontaneous nocturnal, spontaneous early morning, video erotica, etc.) but not others (e.g., partner or spousal attention).

Current diagnosis of and professional thinking on the etiology of male erectile dysfunction has focused on the severity of the condition, i.e., mild, moderate and severe. One method of diagnosis employs oral medication as a means to distinguish dysfunctional patients who can respond to oral medications from those who require more direct intervention, i.e., such as intracavernosal injection or surgery.

Oral medicines, are particularly desirable and sought after discreet forms of treatment. See, for example, Leland J., "A Pill for Impotence?", *Newsweek*, pp. 62–68 (Nov. 17, 1997).

Apomorphine, a selective dopamine receptor agonist, has been widely utilized as an emetic agent, sedative, antiparkinsonian agent and a behavior altering agent and previously was shown to have very poor oral bioavailability. See, for example, Baldessarini et al., in Gessa et al., eds., *Apomorphine and Other Dopaminomimetics, Basic Pharmacology*, 1, pp. 219–228, Raven Press, N.Y. (1981). However, recent research and clinical studies of the effect of orally administered apomorphine on penile tumescence in male patients afflicted with psychogenic impotence show that oral administration of apomorphine can indeed induce an erection in a psychogenic male patient in response to physical sexual stimulation. The specific mechanisms by which apomorphine acts to produce an erectile response in a human male are not yet completely understood, but are believed to be centrally acting through dopamine receptor stimulation in the medial preoptic area of the brain.

While apomorphine can be orally administered in an effective dose, the dose required to achieve a significant erectile response must not be accompanied by substantial nausea and vomiting, or other undesirable side effects, such as arterial hypotension, flushing and diaphoresis (sweating). At dosages of more than 6 milligrams, for example, in some instances the level of accompanying nausea and vomiting interferes with the benefit in treating male erectile dysfunction with apomorphine.

During normal penile erections, when the inflow of blood to the corpora cavernosa engages the sinusoidal spaces, the trabecular tissue compresses small cavernosal veins against the thick fibrous tissue surrounding the corpora to maintain the erection. To mediate these changes in blood flow, nitric oxide is released from postsynaptic parasympathetic neurons and, to a lesser extent, endothelial cells and α-adrenergic neurons are inhibited in the arterial and trabecular smooth muscle. Nitric oxide, which is readily diffusible, stimulates the formation of increased cyclic guanosine monophosphate (GMP) in the corpus cavernosum by guanylate cyclase to relax the smooth muscle cells.

Recently, the oral use of the citrate salt of sildenafil has been approved by the U.S. Food and Drug Administration (FDA) for the treatment of male erectile dysfunction. Sildenafil is reported to be a selective inhibitor of cyclic-GMP-specific phosphodiesterase type 5 (PDE5), the predominant isozyme metabolizing cyclic GMP formed in the corpus cavernosum. Since sildenafil is a potent inhibitor of PDE5 in the corpus cavernosum, it is believed to enhance the effect of nitric oxide, thereby increasing cavernosal blood flow in the penis, especially with sexual stimulation. Inasmuch as sildenafil at the currently recommended doses of 25–100 mg has little effect in the absence of sexual stimulation, sildenafil is believed to restore the natural erectile response to sexual stimulation but not cause erections in the absence of such stimulation. See, for example, Goldstein et al., "Oral Sildenafil in the Treatment of Erectile Dysfunction," *The New England Journal of Medicine*, 338, pp 1397–1404 (1998). The localized mechanism by which cyclic GMP stimulates relaxation of the smooth muscles has not been elucidated.

In dose-response studies, increasing doses of sildenafil (25 to 100 mg) reportedly increased the erectogenic efficacy of sildenafil. However, the oral administration of sildenafil is also accompanied by dose-responsive undesirable side effects. Consequently, at dosages higher than 50 milligrams, the incidence of such side effects as abnormal vision problems ranging from blue or green halo effects to blurring, dyspepsia, nasal congestion, blinding headaches, flushing redness, diarrhea, dizziness, rash, and urinary tract infection increases.

Other more serious side effects have been reported, such as syncope (loss of consciousness), priapism (erection lasting 4 hours or more) and increased cardiac risk (coital coronaries), can be brought on in some cases by physiological predisposition, adverse drug interaction or potentiation, or by drug abuse. In particular, hypotension crisis can result from the combination of sildenafil citrate and organic nitrates, causing, in some cases death, so its administration to patients who are concurrently using organic nitrates (such as nitroglycerin) in any form is contraindicated. Moreover, the long-term effects of large doses of sildenafil containing drugs is not known. See, for example, Handy B., "The Viagra™ Craze," *Time*, pp 50–57 (May 4, 1998).

Some attempts have been made to treat sexual dysfunction in females caused by hysterectomy, menopause and vascular disorders, like diabetes, by employing topical gels containing Viagra™. See, for example, Valdes-Rodriguez, A, "Viagra for her," *Chicago Tribune*, Womanews Section 13, p 7 (Dec. 20, 1998).

Thus there is an ongoing need and desire for a discreet, convenient treatment of sexual dysfunction in humans, suitable for men or women, and preferably for oral delivery systems without the incidence or likelihood of undesirable attendant side effects.

SUMMARY OF THE INVENTION

The present invention provides a therapy regimen of oral administration of apomorphine and sildenafil compositions. Apomorphine and sildenafil can be either co-administered or administered sequentially, prior to sexual activity. A practical therapeutic delivery system is provided employing apomorphine and sildenafil which system sustains satisfaction during sexual activity; i.e., it optimizes the erectile penile response in human males and clitoral response in females to sexual stimuli while minimizing the undesirable side effects associated individually therewith. The oral compositions are preferably administered in sublingual dosage forms.

In one composition embodiment suitable for oral therapy, apomorphine and sildenafil can be concurrently co-administered as a combination sublingual dosage unit. Sublingual combination dosage units preferably contain apomorphine in the range of about 1 to about 6 milligrams (mg) and sildenafil in the range of about 10 to about 75 mg, so long as the final dosage combination received by the patient is accompanied by minimal or substantially no undesirable side effects. A preferred sublingual combination dosage unit contains about 2 mg apomorphine and about 15 to about 50 mg sildenafil.

For sequential administration therapy, apomorphine and sildenafil are administered in separate dosage units each of which employs a lesser dosage amount of the respective drug than is required for achieving the same level of erectile response when it is used as the sole active medicament. Composition embodiments suitable for sequential administration of sildenafil and apomorphine, preferably each in sublingual dosage form, preferably contain sildenafil in a range of about 10 to about 75 mg, more preferably in the range of about 15 to about 50 mg, and apomorphine in a range of about 1 to not more than 6 mg, more preferably in the range of about 2 to about 5 mg so long as the total dose combination received by the patient is accompanied by minimal or substantially no undesirable side effects.

The administration of apomorphine and sildenafil, either co-administered or administered sequentially, beneficially provides a discreet, convenient therapy regimen for effectively achieving and maintaining erections sufficient for vaginal penetration in response to physical sexual stimuli within a practical therapy period.

For co-administration of sildenafil and apomorphine, the combination dosage unit preferably is taken by a male patient suffering from erectile dysfunction about 20–45 minutes before sexual activity to achieve and maintain an erection of sufficient rigidity for vaginal penetration with substantially no attendant adverse side effects, most notably, substantially no nausea and vomiting.

For sequential administration, the male patient preferably takes one dosage unit of sildenafil containing the appropriate sildenafil dosage and one dosage unit of apomorphine containing the appropriate apomorphine dosage substantially within 30–60 minutes of one another and within 15–30 minutes prior to sexual activity.

It has now been found that an oral therapy regimen employing apomorphine and sildenafil in combination with one another can effectively optimize the initiation and maintenance of penile erection in response to sexual stimuli and minimize the side effects associated with each respective medicament. Moreover optimization is achieved at dosage levels below the efficacy levels required in oral therapies employing each drug as the sole medicament.

Further, apomorphine and sildenafil can also be combined, for concurrent or sequential administration therapies, with lesser amounts of erectogenic agents selected from adrenal steroids, such as testosterone, dehydroepiandrosterone (DHEA), and the like; alpha receptor blockers, such as phentolamine, yohimbine, prazosin, doxazosin, terazosin, trimazosin, and the like; or peripheral vasodilators, such as prostaglandin $E_1$ (alprostadil), and like smooth muscle relaxants. Preferably, the erectogenic agents are added in an amount in the range of about 50 to about 100 percent by weight of the weight of apomorphine administered.

Advantageously, practicing the method of this invention, avoids or minimizes the possibility of abusive use of sildenafil because the emetic effect of increased apomorphine ingestion makes the combination substantially self-limiting.

DETAILED DESCRIPTION OF PREFERRED EMBODIMENTS

Apomorphine is a dopamine receptor agonist that has a recognized use as an emetic when administered subcutaneously in about a 5-milligram dose. For the purposes of the present invention, apomorphine or a similarly acting dopamine receptor agonist, is administered in an amount sufficient to excite cells in the mid-brain region of the patient but with minimal side effects. This cell excitation is believed to be part of a cascade of stimulation that is likely to include neurotransmission with serotonin and oxytocin and which initiates erection upon physical sexual stimulation.

The dopamine receptors in the mid-brain region of a patient can be stimulated to a degree sufficient to cause an erection by the sublingual administration of apomorphine. Apomorphine, also known by the chemical name (R)-5,6,6a,7-tetrahydro-6-methyl-4H-dibenzo-[de,g] quinoline-10,11-diol, has the following chemical structure:

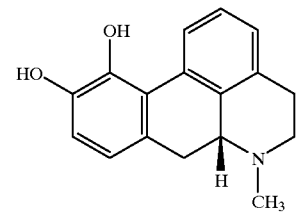

Apomorphine exists in a free base form or as an acid addition salt. For the purposes of the present invention apomorphine hydrochloride is preferred; however, other pharmacologically acceptable moieties thereof can be utilized as well. The term "apomorphine" as used herein includes the free base form of this compound as well as the pharmacologically acceptable acid addition salts thereof. In addition to the hydrochloride salt, other acceptable acid addition salts are the hydrobromide, the hydroiodide, the bisulfate, the phosphate, the acid phosphate, the lactate, the citrate, the tartarate, the salicylate, the succinate, the maleate, the gluconate, and the like.

Sublingual administration of apomorphine preferably takes place over a time period in the range of about 2 to about 10 minutes, or longer. When apomorphine is the sole therapeutic agent, the amount of apomorphine administered sublingually over this time period preferably is in the range of about 5 to about 74 micrograms per kilogram (µg/kg) of the patient's body weight, and most preferably within the range of about 50 to about 74 µg/kg of body weight.

A maximum plasma concentration ($C_{max}$) of the apomorphine drug at which the onset of adverse effects, such as nausea, occur in human male subjects is at a threshold $C_{max}$ of about 2.5 nanograms/milliliter (ng/ml). Plasma concentration is preferably maintained at no more than 5.5 ng/ml during sexual activity, when apomorphine is the sole active agent.

Sildenafil is designated chemically as 1-[[3-(6,7-dihydro-1-methyl-7-oxo-3-propyl-1H-pyrazolo[4,3-d] pyrimidin-5-yl)-4-ethoxyphenyl]sulfonyl]-4-methyl piperazine and has the following structural formula:

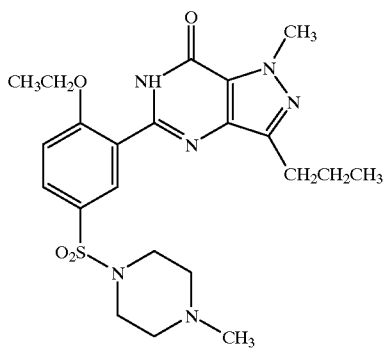

The term "sildenafil" as used herein includes the free base form of this compound as well as pharmacologically acceptable acid addition salts thereof formed with organo-carboxylic acids, organo-sulphonic acids or inorganic acids. For purposes of the present invention, the organo-carboxylic acid salt, sildenafil citrate, having a solubility in water of 3.5 mg/ml is particularly preferred. Reference to "sildenafil" includes sildenafil citrate.

Sildenafil citrate is presently the active ingredient of a commercial medication for impotence sold under the designation Viagra™ (Pfizer Labs, N.Y.) formulated in tablets equivalent to 25 mg, 50 mg and 100 mg sildenafil for oral administration. According to the manufacturer, in addition to the active ingredient, sildenafil citrate, each tablet contains the following inactive ingredients: microcrystalline cellulose, anhydrous dibasic calcium phosphate, croscarmellose sodium, magnesium stearate, hydroxypropyl methylcellulose, titanium dioxide, lactose, triacetin, and FD&C Blue #2 aluminum lake.

It is known from in vitro studies that sildenafil is approximately 4,000 fold more selective for inhibiting phosphodiesterase type 5 (PDE5) than on other known phosphodiesterases, such as PDE3, which is involved in control of cardiac contractility. Sildenafil is reportedly only about 10-fold as potent for PDE5 compared to PDE6, an enzyme found in the retina and it is this lower selectivity which is thought to be the basis for abnormalities related to color vision observed with higher doses or plasma levels.

Sildenafil, administered as the commercially available Viagra™ formulation, is reported to be rapidly absorbed after oral administration, with absolute bioavailability of about 40%. Its pharmacokinetics are dose-proportional over the recommended dose range. Based on the Viagra™ manufacturer's product literature, maximum observed plasma concentrations are reached within 30 to 120 minutes (median 60 minutes) of oral dosing in the fasted state. When the Viagra™ formulation is taken with a high fat meal, the rate of absorption is reduced, with a mean delay in Tmax of 60 minutes and mean reduction in Cmax of 29%. The mean steady state volume of distribution (Vss) for sildenafil is reportedly 105 L, indicating distribution into the tissues. Based upon reported measurements of sildenafil in the semen of healthy volunteers 90 minutes after dosing, less than 0.001% of the administered dose appeared in the semen of the patients.

Ordinarily when higher doses of apomorphine alone are administered sublingually, apomorphine is administered preferably about 15 to about 20 minutes prior to sexual activity to affect that part of the brain that initiates erection and when higher doses of sildenafil alone are administered, sildenafil is taken about 1 hour or more before sexual stimulation to induces smooth muscle cell relaxation for maintaining an erection. Surprisingly, a therapeutically effective dosage combination of apomorphine and sildenafil employed with the compositions of this invention maximizes the beneficial erectogenic efficacy of both apomorphine and sildenafil at dosages of each drug substantially lower than required respectively and substantially minimizes nausea or undesirable side effects associated with such dosages.

Illustrative preferred sublingual dosage forms for co-administration of apomorphine are set forth in Table I, below.

Sublingual combination dosage units preferably contain apomorphine in the range of about 1 to not more than 6 milligrams (mg), preferably in the range of about 2 and about 5 mg and of sildenafil in the range of about 10 to about 75 mg, preferably in the range of about 15 to about 50 mg, so long as the combined dose received by the patient is accompanied by minimal or substantially no undesirable side effects. A particularly preferred sublingual combination dosage unit contains about 2 mg apomorphine and not more than 50 mg sildenafil, more preferably about 2 mg apomorphine and not more than about 25 mg sildenafil.

Alternatively, the apomorphine and sildenafil may be formulated separately in the foregoing compositions as the sole active ingredient for practicing sequential administration of each respective drug.

For sequential administration therapy, sildenafil and apomorphine each is administered in a separate dosage unit containing a lesser dosage amount of respective drug than is required for achieving the same level of erectile response when the drug is the sole medicament. For sequential administration of sildenafil, the dosage unit preferably contains sildenafil in a range of about 10 to about 75 mg, more preferably in the range of about 15 to about 50 mg, and for administration of apomorphine the dosage unit preferably contains apomorphine in a range of about 1 to not more than 6 mg, more preferably in the range of about 2 to about 5 mg so long as the total combined dose received by the patient is accompanied by minimal or substantially no undesirable side effects.

A particularly preferred sequential administration dosage unit of sildenafil contains sildenafil in the range of about 15 to about 35 mg and of apomorphine contains apomorphine in the range of about 2 to about 4 mg. Preferably, each drug is administered sublingually. Alternatively, each drug can be administered by different oral routes; i.e., one can be ingested and the other administered sublingually or by buccal patch.

Preferably, sublingual dosage forms dissolve within a time period of at least about 2 minutes but less than about 10 minutes. The dissolution time can be longer, however, if desired as long as the necessary plasma concentration of apomorphine and sildenafil can be maintained. More preferably, the dissolution time in water for the presently contemplated dosage forms is about 3 minutes to about 5 minutes.

If desired, to facilitate absorption and thus bioavailability, absorption enhancing agents, such as cyclodextrins, particularly β-cyclodextrin, or a derivative thereof, such as hydroxypropyl-β-cyclodextrin (HPBCD) and the like may be included. Cyclodextrins are a group of cyclic, nonreducing oligosaccharides built up from six, seven or eight glucopyranose rings, respectively known as alpha, beta and gamma cyclodextrins. The cyclodextrins are a class of cavity-containing cyclic compounds possessing the property of forming a molecular inclusion complexes, which anchor or entrap another chemical compounds without the formation of covalent bonds. HPBCD is a cyclic polymer having a doughnut-shaped molecular structure including an inner cavity, as shown below:

preferably in the range of about 1 to about 10 weight percent of the total composition.

Particularly in the case of sildenafil, it has been found that HPBCD enhances bioavailability. Thus, the desired therapeutic effect can be achieved with a relatively lower dose of sildenafil, thereby minimizing the likelihood of adverse affects.

For effective sequential administration of sildenafil and apomorphine, the release of each drug is preferably staggered to maximize the beneficial inducement of erection by apomorphine and maintenance of erection by sildenafil upon sexual stimulation.

To augment the beneficial effect of apomorphine and sildenafil therapy, lesser amounts of erectogenic agents can be included. The term "erectogenic agents" as used herein refers to adrenal steroids, such as testosterone, dehydroepiandrosterone (DHEA) and the like; alpha receptor blockers, such as phentolamine, yohimbine, prazosin, doxazosin, terazosin, trimazosin and the like; or peripheral vasodilators, such as prostaglandin $E_1$ (alprostadil) and like smooth muscle relaxants that are know to improve the blood flow in the vascular system. Preferably, the erectogenic agents are

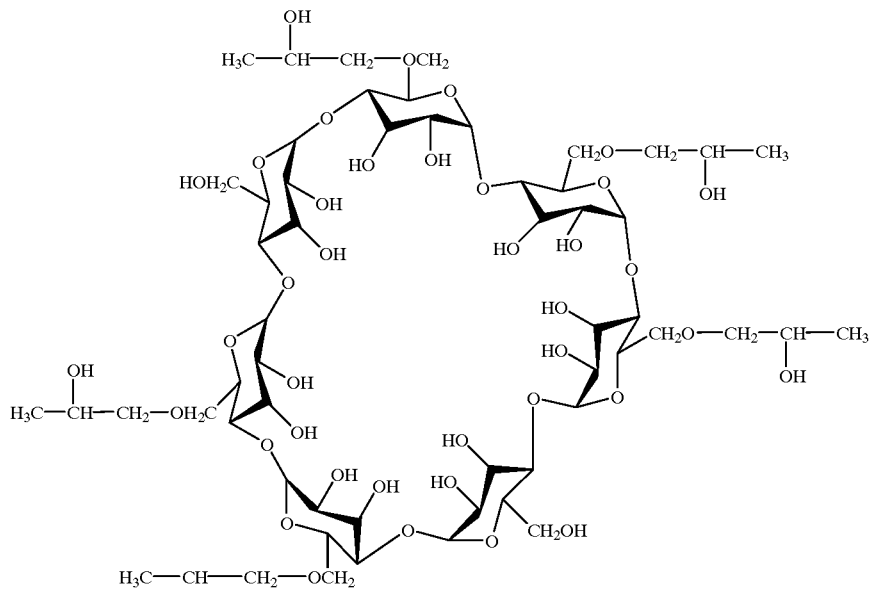

Hydroxypropyl-β-cyclodextrins are commercially available compounds that are derived from β-cyclodextrins by condensation with a propylene oxide to provide the corresponding hydroxypropyl derivatives having a degree of substitution (D.S.) of up to about 15 or higher. For the purposes of the present invention a D.S. value of about 5 to 7 is preferred.

The preparation of such suitable hydroxypropyl-β-cyclodextrins is described, inter alia, in the *International Journal of Pharmaceutics*, 29, 73–82 (1986) and in the *Journal of Pharmaceutical Sciences*, 75 (6), 571–572 (1986). Also known and suitable for the present invention are the hydroxypropyl-β-cyclodextrins that are polyethers of cyclodextrins and are obtained by the condensation of an excess of hydroxypropylene oxide with β-cyclodextrin as described in U.S. Pat. No. 3,459,731. to Gramera et al. Hydroxypropyl-β-cyclodextrin (HPBCD) is particularly preferred cyclodextrin constituent, but is not limited thereto. The weight percent of the HPBCD in the composition is added in an amount in the range of about 50 to about 100 percent by weight, more preferably in the range of about 60 to about 80 percent by weight of the weight of apomorphine administered.

While nausea from the use of the inventive combination of apomorphine and sildenafil is unlikely, the onset of nausea, should it occur, can also be substantially obviated or delayed by including an antiemetic agent. Antiemetic agents are antinauseant drugs that prevent or substantially reduce nausea and vomiting. As used herein, the terms "antiemetic agent" and "antinausea agent" are interchangeable and mean a pharmaceutically acceptable compound that substantially reduces nausea symptoms.

Antiemetic agents that can be used in conjunction with apomorphine in the present compositions are antidopaminergic agents, such as the benzamides, e.g., metoclopramide, trimethobenzamide, benzquinamid, and the like; the phenothiazines, e.g., chlorpromazine, prochlorperazine, pipamazine, thiethylperazine, oxypendyl hydrochloride, promazine, triflupromazine, propiomazine, acepromazine, acetophenazine, butaperazine, carphenazine, fluphenazine, perphenazine, thiopropazate, trifluoperazine, mesoridazine, piperacetazine, thioridazine, pipotiazine, pipotiazine palmitate, chlorprothixine, thiothixine, doxepin, loxapin, triflupromazine, methdilazine, trimeprazine, methotrimeprazine, and the like; serotonin (5-hydroxytryptamine or 5-HT) antagonists such as domperidone, odansetron (commercially available as the hydrochloride salt under the designation Zofran®), and the like; the histamine antagonists such as buclizine hydrochloride, cyclizine hydrochloride, dimenhydrinate (Dramamine), and the like; the parasympathetic depressants such as scopolamine, and the like; other antiemetics such as metopimazine, trimethobenzamide, benzquinamine hydrochloride, diphenidol hydrochloride, and the like; and piperazines, such as meclizine, chlorcyclizine and the like. Antiemetic containing apomorphine compositions are described in co-pending U.S. patent application Ser. No. 09/138,982, filed on Aug. 24, 1998, the description thereof is incorporated herein by reference to the extent pertinent.

The likelihood of the onset of nausea can also be substantially obviated or delayed by including in the formulation a ganglionic agent (inhibitor of ganglionic response), or certain ganglionic stimulating alkaloids, such as nicotine or lobeline, preferably as lobeline sulfate, which can serve as antiemetic agents.

The present invention may be illustrated by studies with participating male patients selected on the basis of their response to a Baseline Sexual History Questionnaire shown below as initially presenting with a complaint of impotence or erectile dysfunction. Instructions are given regarding the protocol to be followed by the volunteer patients in a home use trial employing sublingual tablets and informed consent is obtained. Patients are advised that they are free to withdraw from the trial at any time without penalty or prejudice. During the home use trial, the volunteer male patients are asked to fill out a Sexual Function Study Home Questionnaire shown below in Example 2.

---

BASELINE SEXUAL HISTORY QUESTIONNAIRE
Male

---

Initials: _____ Subject#: _____ Today's Date: _____ Time: _____
                              Date Tablet Taken: _____ Time: _____
Each line below represent the full range of feeling or response.
Please mark each line clearly with a vertical (straight up and down) stroke at the point which represents your response.
(There are no right or wrong answers. Do not write in boxes on right.)
1. Rate your overall (on the average) level of satisfaction with your sexual performance within the past two months.
   Extremely                                         Extremely
   Unsatisfied    _____   Satisfied [ ]
2. What was your level of satisfaction with your most recent attempt at sexual intercourse with your wife/partner?
   Extremely                                         Extremely
   Unsatisfied    _____   Satisfied [ ]
3. What were the results of your erection during your most recent attempt at sexual intercourse with your wife/partner?
                                                     Rigid Erection
   No                                                Suitable for
   Erection       _____   Penetration [ ]
4. What are your overall (on the average) erection results when you attempt sexual intercourse?
                                                     Rigid Erections
   No                                                Suitable for
   Erection       _____   Penetration [ ]
5. Were your successful in completing sexual    [ ] Yes  [ ] No
   intercourse during your most recent attempt?
6. On the average, how frequently do you attempt sexual intercourse?

---

-continued

BASELINE SEXUAL HISTORY QUESTIONNAIRE
Male

---

(Pease circle one answer)
1) rarely or never            5) 4 to 5 times a month
2) 2 to 6 times a years       6) 6 to 8 times a month
3) once a month               7) more than 8 times a month
4) 2 to 3 times a month

---

The present invention is illustrated further by the following Examples.

EXAMPLE 1

Sublingual Tablets

This example illustrates the preparation of sublingual (SL) tablets dosage forms tablets suitable for oral co-administration of apomorphine and sildenafil.

A series of SL tablets were prepared as combination dosage units to contain apomorphine in a range of 2 to 6 mg and sildenafil in a range of 15 to 35 mg as shown below. For purposes of illustration and not as limitation, the SL tablets were prepared by grinding tablets of the Viagra™ formulation (50 mg) to a powder, blending the Viagra™ powder with apomorphine and conventional excipients, and compressing the mixture to tablet form.

| Apomorphine HCl (mg) | Sildenafil (mg) | # of Tablets |
| --- | --- | --- |
| 2 | 15 | 10 |
| 2 | 25 | 10 |
| 2 | 35 | 10 |
| 4 | 35 | 5 |
| 6 | 35 | 5 |

EXAMPLE 2

Home-Use Trial

This example illustrates the oral co-administration of apomorphine and sildenafil by sublingual (SL) tablet dosage forms by four healthy male volunteer patients, ranging in age from 36 to 54 years, in an informal home-use trial.

The following Tablet nos. 1–6 were prepared containing the amounts of drug indicated to be taken sublingually (SL) or conventionally ingested (oral) as instructed:

Tablet No. 1: SL placebo.

Tablet No. 2: SL (2 mg) apomorphine.

Tablet No. 3: Oral (50 mg) sildenafil.

Tablet No. 4: SL comination of (2 mg) apomorphine and (20 mg) sildenafil.

Tablet No. 5: SL (20 mg) sildenafil solid dispersion (sd) prepared as described below.

Tablet No. 6: SL (20 mg) sildenafil with added hydroxypropyl-beta-cyclodextrin (HPBCD) at about 10% by weight of the total composition prepared as described below.

Preparation of Tablet No. 5: Sildenafil citrate (250 mg) was dissolved in ethanol (100 ml, 90%). PEG 8000 (polyethylene glycol, 8,000 molecular weight) was then added and dissolved. The resulting ethanol solution was incubated at room temperature for about 2 hours and then evaporated under reduced pressure to solid dispersion. 2.6 Grams of the resulting solid dispersion was blended with 50 mg sweetener (acesulfame K), 400 mg avicel, 30 mg peppermint flavor, 20 mg. chocolate flavor and 100 mg magnesium stearate. Ten tablets, each having an average weight of about 322 mg and an average hardness of about 6 Kp, were prepared by manual compression employing a 1×0.5 cm. oval die.

Preparation of Tablet No. 6: Sildenafil citrate (250 mg) was dissolved in ethanol (50 ml, abs.). HPBCD (551.2 mg) was then added and dissolved to provide a 1:1 molar ratio of HPBCD:sildenafil. The resulting ethanol solution was incubated at room temperature for about 2 hours and then evaporated under reduced vacuum pressure to form a white to off white free flowing powder. 640 Grams of the resulting powder was blended with 50 mg sweetener (acesulfame K), 350 mg avicel, 30 mg peppermint flavor, 20 mg. chocolate flavor, 380 mg mannitol powder, and 30 mg magnesium. stearate. Ten tablets, each having an average weight of about 155 mg and average hardness of about 5 Kp were prepared by manual compression employing a 1×0.5 cm. oval die.

Each volunteer patient was randomized to receive at least one treatment, preferably two treatments, with each one of the Tablets, Nos. 1–6, over a twelve week period. The volunteer patient was instructed to attempt coitus at least once a week and to take, prior to doing so, a single tablet sublingually (or orally as indicated for Tablet no. 3) on the first attempt, and on each subsequent attempt taking a single tablet from the numbered packet.

Each patient was instructed to complete a Sexual Function questionnaire shown below within 24 hours of using a tablet. In response to question 1 on the questionnaire, the patient's erection/sexual satisfaction was to be marked along a 10 cm line scored from left to right (0–10). The scores summarized for each of patient A (53 years old); B (36 years old); C (52 years old); and D (54 years old) at the end of the trial are shown in Table 1.

SEXUAL FUNCTION STUDY HOME QUESTIONNAIRE - Male

Please answer questions within 12–24 hours of taking sublingual tablet.
Initials: _____ Subject#: _____ Today's Date: _____ Time: _____
Date Tablet Taken: _____ Time: _____
The lines below represent the full range of feeling or response.
Please mark each line clearly with a vertical (straight up and down) stroke at the point which represents your response.
(There are no right or wrong answers. Do not write in boxes on right.)

1. What was your erection result after taking the sublingual tablet?
   No Erection — Rigid Erection Suitable for Penetration [ ]

2. Did you have intercourse with [ ] Yes [ ] No
   wife/partner after taking tablet?
   IF NO.          0 - No erection.
   please circle   1 - Erection not sufficient for penetration.
   all reasons     2 - Felt sick after taking tablet.
   that apply:        (Describe below in #4.)
                   3 - I decided not to participate in intercourse.
                   4 - Wife/partner decided not to participate.
                   5 - Unrelated interruption (example, telephone call).
                   6 - Wife/partner menstruating.
                   7 - Other, explain: _____

3. What was your level of satisfaction with this attempt at sexual intercourse?
   Extremely Unsatisfied — Extremely Satisfied [ ]

4. Please describe any adverse reactions you experienced after taking the sublingual tablet. (Indicate when the reaction started and stopped, and any intervention taken i.e. "nosebleed on 5/1/94, used a cold compress".)
   _____
   _____
   _____

5. Other comments?
   _____
   _____

TABLE 1

ERECTION/SEXUAL SATISFACTION SCORES

Score First score = scale of 0–10 erection result after taking tablet sublingually (SL) or conventionally (oral)
(0 = No erection; 6 = Rigid erection suitable for penetration; 10 = Optimum erection)
Second score = scale of 0–10 level of satisfaction with this attempt at sexual intercourse
(0 = extremely unsatisfied; 10 = extremely satisfied).
If the second score is a dash (—), sexual intercourse was not attempted.
(•) = No data for this treatment.

| Patient Age | SL Tablet No. 1 Placebo | SL Tablet No. 1 Placebo | SL Tablet No. 2 2 mg Apo | SL Tablet No. 2 2 mg Apo | Oral Tablet No. 3 50 mg SD | Oral Tablet No. 3 50 mg SD | SL Tablet No. 4 2 mg apo/ 15 mg SD | SL Tablet No. 4 2 mg apo/ 15 mg SD | SL Tablet No. 5 20 mg SD-sd | SL Tablet No. 5 20 mg SD-sd | SL Tablet No. 6 20 mg SD With HPBCD | SL Tablet No. 6 20 mg SD With HPBCD |
|---|---|---|---|---|---|---|---|---|---|---|---|---|
| A 53 y | 10/10 | 10/10 | 10/10 | 10/10 | 10/10 | 10/10 | 10/10 | 10/10 | 10/10 | 10/10 | 10/10 | • |
| B 36 y | 10/8 | 8/8 | 10/4 | 10/5 | 10/8 | 10/9 | 10/10 | 10/10 | 10/10 | 10/10 | 10/10 | 10/10 |
| C 52 y | 0/— | 0/— | 9/9.5 | 1/.5 | 8.5/8.5 | 1.5/1.5 | 10/10 | 10/10 | 0/— | 9.5/8 | 8/8 | 7.5/6 |
| D 54 y | 8/— | • | 9/9 | | 8/6 | • | 3/— | • | 3.5/— | • | 8/8.5 | • |

Apo - Apomorphine HCl
SD - Sildenafil
HPBCD - Hydroxypropyl-beta-cyclodextrin
sd-solid dispersion The scores from patients B and C showed that the combination of 2 mg apomorphine and 15 mg sildenafil taken sublingually (tablet no. 4) produced optimal erection and satisfaction levels, greater than those produced by sublingually administered 2 mg apomorphine alone (table no. 2) or higher amounts (50 mg) of conventionally administered (oral) sildenafil (tablet no. 3). The scores from patients B and C also showed that erection/satisfaction equal to or greater than that produced by 50 mg sildenafil (tablet no. 3) taken orally was achieved with lesser amounts (20 mg) of sildenafil taken sublingually (tablet nos. 5 and 6). The data from patients C and D, indicated some enhancement of the erection/sexual satisfaction scores obtained with sublingual 20 mg sildenafil by including HPBCD (tablet no. 6) over that obtained with sublingual 20 mg sildenafil alone (table no. 5). The data from patient A indicates that no negative decrease in erection/sexual satisfaction was produced by the use of either apomorphine, sildenafil or a combination thereof.

EXAMPLE 3
Direct Compression Compositions

This example illustrates SL tablet A, B, and C compositions shown in Table 2 prepared by direct compression method.

TABLE 2

| Direct Compression Compositions | | | |
|---|---|---|---|
| Ingredient (mg/tablet) | A | B | C |
| Apomorphine HCl, USP | 2 | 2 | 2 |
| Sildenafil Citrate, USP | 15 | 15 | 15 |
| Ascorbic Acid, USP | 3 | 3 | 3 |
| Citric Acid, Anhydrous, NF | 2 | 2 | 2 |
| Microcrystalline Cellulose, NF (Avicel PH102) | 22.7 | 22.7 | 22.7 |
| Magnesium Stearate, NF | 1.2 | 1.2 | 1.2 |
| Hydroxypropyl methylcellulose (Methocel E4M Premium, NF) | 5 | 5 | 5 |
| D&C Yellow 10 Aluminum Lake, NF | 0.1 | 0.1 | 0.1 |
| Aspartame, USP | 1 | 1 | 1 |
| Mannitol, USP, powder | 21 | 19 | 17 |
| TOTAL, mg/tablet | 73 | 71 | 69 |

Composition A is prepared by weighing the amounts of the ingredients listed in Table 2. Each ingredient is passed through an appropriate sized (30 mesh) screen. The apomorphine HCl, sildenafil citrate, ascorbic acid, aspartame, D&C yellow 10 Lake, and the citric acid are placed into a blender and blended for 5 minutes. Hydroxypropyl methylcellulose (Methocel E4M, Premium) is added to the blender and mixing is continued for an additional 5 minutes. Microcrystalline cellulose (Avicel PH102) is then added to the blender and mixing is continued for an additional 5 minutes. Next, the mannitol is added to the blender and mixed for an additional 5 minutes. Finally, the magnesium stearate is added to the blender and mixed for an additional 2 minutes to yield a final powder mix. The final powder mix is transferred to a suitable tableting machine equipped with the appropriate sized tooling and compressed into tablets.

Compositions B and C are prepared by following the procedure of Composition A, except for the amounts of ingredients as indicated.

EXAMPLE 4
Wet Granulation Compositions

This example illustrates SL tablet compositions D–J shown in Table 3 below prepared by wet granulation method.

TABLE 3

| Wet Granulation Compositions | | | | | | | |
|---|---|---|---|---|---|---|---|
| INGREDIENT (mg/tablet) | D | E | F | G | H | I | J |
| Apomorphine Hcl, USP | 2 | 2 | 2 | 2 | 2 | 2 | 2 |
| Sildenafil Citrate, USP | 15 | 15 | 15 | 15 | 15 | 15 | 15 |
| Ascorbic Acid, USP | 3 | 3 | 3 | 3 | 3 | 3 | 3 |
| Citric Acid, Anhydrous, NF | 2 | 2 | 2 | 2 | 2 | 2 | 2 |
| Microcrystalline Cellulose, NF (Avicel PH102) | 40 | 40 | 40 | 40 | 40 | 40 | 40 |
| Magnesium Stearate, NF | 1 | 1 | 1 | 1 | 1 | 1 | 1 |
| Aspartame, USP | 1 | 1 | 1 | 1 | 1 | 1 | — |
| Mannitol, USP, powder | 42 | 42 | 42 | 42 | 42 | 42 | 42 |
| Carbomer (Carbopol 974P) | 10 | — | — | — | — | — | — |
| Sodium Alginate | — | 5 | 10 | — | — | — | — |
| Gelatin, NF | — | — | — | 10 | — | — | — |
| Sodium Carboxymethyl Cellulose | — | — | — | — | 10 | — | — |
| Gum Tragacanth, NF | — | — | — | — | — | 10 | — |
| Hydroxypropyl methylcellulose (Methocel E4M, NF) | — | — | — | — | — | — | 10 |
| TOTAL, mg/tablet | 116 | 111 | 116 | 116 | 116 | 116 | 116 |

Composition D is prepared from the ingredients listed in Table 3 employing the water dispersible polymer, carbomer, Carbopol 974P. Each ingredient is weighed as indicated. A solution containing apomorphine HCl, sildenafil citrate, citric acid, and ascorbic acid is prepared by dissolving the ingredients into a mixture of equal volumes of purified water and ethanol, USP. The solution is warmed slightly, and mannitol is added. The solution is mixed until clear, then absorbed onto the microcrystalline cellulose to form a mass. The mass is mixed in a stainless steel pan until uniform. The mass is granulated by screening through a #8 mesh screen and then dried at about 60 to about 70 degrees Celsius for about 4 hours. The mass is mixed periodically during this drying step.

The resultant dried granules are passed through a 32 mesh screen. The appropriate polymers and aspartame are blended with the dried granules for a period of about 5 minutes using a twin shell V-shaped blender. At the end of the blending cycle magnesium stearate is added to the blender and the blending is continued for an additional 2 minutes to produce a final mix.

The final mix is removed from the blender and fed into a Stoke's single punch tablet press fitted with fitted with biconvex 7/32" diameter tooling for tablet preparation. Tablets may be prepared at various compression forces, yielding tablets of different hardnesses.

Except for employing the water dispersible polymer listed in Table 3, Compositions E–J may be prepared by following the procedure for Composition D.

EXAMPLE 5
Wet Granulation Compositions

This example further illustrates SL tablets K–Q shown in Table 4 below employing various water-dispersible compounds prepared by wet granulation method.

TABLE 4

Other Wet Granulation Compositions

| INGREDIENT (mg/tablet) | K | L | M | N | O | P | Q |
| --- | --- | --- | --- | --- | --- | --- | --- |
| Apomorphine HCl, USP | 2 | 2 | 2 | 2 | 2 | 2 | 2 |
| Sildenafil Citrate, USP | 15 | 15 | 15 | 15 | 15 | 15 | 15 |
| Ascorbic Acid, USP | 3 | 3 | 3 | 3 | 3 | 3 | 3 |
| Citric Acid, Anhydrous, NF | 2 | 2 | 2 | 2 | 2 | 2 | 2 |
| Microcrystalline Cellulose, NF (Avicel PH102) | 40 | 40 | 40 | 40 | 40 | 40 | 40 |
| Magnesium Stearate, NF | 1 | 1 | 1 | 1 | 1 | 1 | 1 |
| Aspartame, USP | 1 | 1 | 1 | 1 | 1 | 1 | 1 |
| Mannitol, USP, powder | 42 | 42 | 42 | 42 | 42 | 42 | 42 |
| Polyvinyl pyrrolidone | 10 | — | — | — | — | — | — |
| Polyethylene glycol | — | 10 | — | — | — | — | — |
| Sodium Alginate | — | — | 10 | — | 10 | — | 10 |
| Carbomer (Carbopol 974P) | — | — | — | 10 | — | — | — |
| Mint Flavor | — | — | — | — | — | — | 0.2 |
| Ascorbic acid palmitate | — | — | — | — | — | 10 | — |
| TOTAL, mg/tablet | 116 | 116 | 116 | 116 | 116 | 116 | 116 |

The compositions are prepared by weighing the respective amounts of the ingredients listed in Table 4, mixing the ingredients and forming the tablets by the wet granulation method described in Example 4.

EXAMPLE 6
Direct Compression Compositions

This example illustrates further SL tablet compositions R and S shown in Table 5 below prepared by direct compression method.

TABLE 5

Direct Compression Compositions

| Ingredient (mg/tablet) | R | S |
| --- | --- | --- |
| Apomorphine HCl, USP | 20 | 20 |
| Sildenafil, Citrate, USP | 150 | 150 |
| Ascorbic Acid, USP | 7.5 | 8.4 |
| Citric Acid, Anhydrous, NF | 5 | 5.6 |
| Microcrystalline Cellulose, NF (Avicel PH102) | 57 | 39.2 |
| Magnesium Stearate, NF | 3 | 2.8 |
| Hydroxypropyl methylcellulose (Methocel E4M Premium, NF) | 12.5 | 8.4 |
| Turquoise Lake | 3 | 2.8 |
| Aspartame, USP | 2.5 | 2.8 |
| Mannitol, USP, powder | 19.5 | 30 |
| TOTAL, mg/tablet | 280 | 270 |

Compositions R and S are prepared by weighing the respective amounts of the ingredients listed in Table 5, mixing the ingredients and forming tablets by the direct compression method as described in Example 3.

The foregoing discussion and the reported studies are intended as illustrative of the present invention and are not to be taken as limiting. Still other variants within the spirit and scope of this invention are possible and will readily present themselves to those skilled in the art.

I claim:

1. A method suitable for treating erectile dysfunction in a human patient which comprises administering to said patient prior to sexual activity apomorphine or a pharmaceutically acceptable acid addition salt thereof and sildenafil or a pharmaceutically acceptable acid addition salt thereof each being administered in an amount sufficient to induce and maintain an erection adequate for sustaining satisfaction during sexual activity but less than an amount that induces substantial nausea.

2. The method in accordance with claim 1 wherein the apomorphine and sildenafil are co-administered in a single dosage unit comprising about 1 to about 6 mg apomorphine and about 10 to about 75 mg sildenafil.

3. The method in accordance with claim 2 wherein the single dosage unit comprises about 2 to about 5 mg apomorphine and about 15 to about 50 mg sildenafil.

4. The method in accordance with claim 1 wherein the sildenafil and apomorphine is sequentially administered by first administering a dosage unit comprising sildenafil in an amount in the range of about 10 to about 75 mg and then a dosage unit comprising apomorphine in an amount in the range of about 1 to about 6 mg.

5. The method in accordance with claim 4 wherein the amount of administered apomorphine is in a range of about 2 to 5 mg.

6. The method in accordance with claim 4 wherein the amount of administered sildenafil is in a range of about 15 to about 50 mg.

7. The method in accordance with claim 4 wherein the amount of administered apomorphine is in a range of about 2 to about 5 mg and the amount of administered sildenafil is in a range of about 15 to about 50 mg.

8. The method in accordance with claim 4 wherein the sildenafil is administered within about 30–60 minutes of apomorphine administration.

9. The method in accordance with claim 1 wherein the administration is by sublingual route or combinations thereof.

10. A pharmaceutical composition comprising sildenafil and apomorphine in a pharmaceutically acceptable vehicle.

11. The composition of claim 10 wherein the amount of sildenafil is in the range of about 10 to about 25 mg.

12. The composition of claim 10 wherein the amount of apomorphine is in the range of about 1 to about 6 mg.

13. The composition of claim 10 in sublingual or buccal tablet form.

14. A pharmaceutical composition comprising sildenafil and a cyclodextrin in a pharmaceutically acceptable vehicle.

15. The composition of claim 14 wherein the cyclodextrin is hydroxypropyl-beta-cyclodextrin.

16. The composition of claim 15 wherein the amount of sildenafil is about 20 mg and the amount of hydroxypropyl-beta-cyclodextrin is about 1 to about 10% by weight of the total composition.

17. The composition of claim 10 further including erectogenic agents selected from adrenal steroids, alpha receptor blockers, or peripheral vasodilators added at a concentration in the range of about 50 to about 100 percent by weight of the weight of apomorphine.

18. The composition of claim 17 wherein the erectogenic agent is an adrenal steroid selected from the group consisting of testosterone and dehydroepiandrosterone.

19. The composition of claim 17 wherein the erectogenic agent is an alpha receptor blocker selected from the group consisting of phentolamine, yohimbine, prazosin, doxazosin, terazosin, and trimazosin.

20. The composition of claim 17 wherein the erectogenic agent is prostaglandin $E_1$.

* * * * *